United States Patent
Motchkine et al.

(10) Patent No.: US 6,861,646 B2
(45) Date of Patent: Mar. 1, 2005

(54) CYCLONE SAMPLING NOZZLE FOR AN ION MOBILITY SPECTROMETER

(75) Inventors: Viatcheslav S. Motchkine, Moscow (RU); Leonid Y. Krasnobaev, Newton, MA (US); Stephen N. Bunker, Wakefield, MA (US)

(73) Assignee: Implant Sciences Corporation, Wakefield, MA (US)

( * ) Notice: Subject to any disclaimer, the term of this patent is extended or adjusted under 35 U.S.C. 154(b) by 0 days.

(21) Appl. No.: 10/295,010

(22) Filed: Nov. 14, 2002

(65) Prior Publication Data

US 2003/0155506 A1 Aug. 21, 2003

Related U.S. Application Data

(60) Provisional application No. 60/357,394, filed on Feb. 15, 2002, provisional application No. 60/357,618, filed on Feb. 15, 2002, and provisional application No. 60/363,485, filed on Mar. 12, 2002.

(51) Int. Cl.[7] ........................... H01J 49/40; H01J 49/28; B01D 59/44
(52) U.S. Cl. ....................... 250/288; 250/287; 250/294; 250/290; 250/281
(58) Field of Search ................................. 250/281, 288, 250/287, 290, 294, 286

(56) References Cited

U.S. PATENT DOCUMENTS

| | | |
|---|---|---|
| 5,200,614 A * | 4/1993 | Jenkins ........................ 250/286 |
| 5,300,773 A | 4/1994 | Davies |
| 5,338,931 A | 8/1994 | Spangler et al. |
| 5,728,584 A | 3/1998 | Sausa et al. |
| 5,759,859 A | 6/1998 | Sausa |
| 5,826,214 A | 10/1998 | Lieb et al. |
| 5,906,946 A | 5/1999 | Sausa et al. |
| 5,968,837 A | 10/1999 | Döring et al. |
| 6,073,499 A * | 6/2000 | Settles ...................... 73/864.81 |
| 6,177,669 B1 * | 1/2001 | Wells et al. ................. 250/288 |
| 6,236,042 B1 * | 5/2001 | Kato et al. ................... 250/288 |
| 6,239,428 B1 | 5/2001 | Kunz |
| 6,586,732 B2 * | 7/2003 | Lee et al. .................... 250/288 |
| 2003/0116708 A1 * | 6/2003 | De Ia Mora et al. ....... 250/288 |
| 2003/0193338 A1 * | 10/2003 | Krasnobaev et al. ........ 324/464 |

* cited by examiner

Primary Examiner—John R. Lee
Assistant Examiner—Kalimah Fernandez
(74) Attorney, Agent, or Firm—Choate, Hall & Stewart

(57) ABSTRACT

The presence of trace molecules in air may be determined using an ion mobility spectrometer. Such devices may be used in the fields of explosives detection, identification of narcotics, and in applications characterized by the presence of very low airborne concentrations of organic molecules of special interest. The sensitivity of such instruments is dependent on the method of gas sampling utilized. A cyclone sampling nozzle can greatly improve the sampling efficiency, particularly when the sampling needs to be performed at a distance from the air intake. The cyclone sampling nozzle consists of an intake gas flow and a separate coaxial emitted gas flow which is deflected to move with a circular motion.

23 Claims, 3 Drawing Sheets

CYCLONE SAMPLING NOZZLE FOR AN ION MOBILITY SPECTROMETER

CROSS-REFERENCE TO RELATED APPLICATIONS

This application claims benefit and priority from U.S. Provisional Application No. 60/357,394, filed Feb. 15, 2002, U.S. Provisional Application No. 60/357,618, filed Feb. 15, 2002, and U.S. Provisional Application No. 60/363,485, filed Mar. 12, 2002, all of which are incorporated herein by reference.

BACKGROUND OF THE INVENTION

1. Field of the Invention

This invention relates to an ion mobility spectrometry instrument that detects chemicals present as vapors in air or other gases, or liberated as vapors from condensed phases such as particles or solutions and more particularly relates to the sampling of such vapors for injection into the ion source of the ion mobility spectrometer (IMS) when the source of vapors is at a distance from the entrance orifice of the IMS.

2. Description of Related Art

IMS instruments operate on the basis of the time taken by ionized molecules to move through a gas-filled drift region to a current collector while under the influence of an electric field. The ions are created in a gas-filled region called the ion source, which is connected to the drift region through an orifice or a barrier grid. The ion source may use any of a variety of techniques to ionize atoms and molecules. One or more flowing streams of gas enter the ion source through one or more orifices, and the gas may exit through one or more different orifices. At least one of the flowing gas streams entering the ion source includes gas that has been sampled (the "sample gas") from the surrounding atmosphere or other source of vapor to be analyzed.

In some cases, the process of taking a sample begins with an operator rubbing an absorbent substance, such as chemical filter paper, onto the surface to be tested. Particles of the chemical of interest may then be transferred and concentrated on the absorber. This intermediate absorber may then brought to the vicinity of the sampling orifice of the IMS. However, this method of concentrating using an absorbent substance is deficient in that it tends to be relatively slow to implement and is subject to variations in the skill of the operator. Additionally, while the absorber is relatively low in cost, the process of taking a great many samples becomes expensive in that the absorber generally should only be used once to ensure consistent results.

The instrument's sampling method uses a gas pump, which draws the sample gas into the ion source through a tube. For example, the pump may be disposed to provide a partial vacuum at the exit of the ion source. This partial vacuum may be transmitted through the confines of the ion source and appear at the entrance orifice of the ion source. A further tubulation may be provided as an extension to a more conveniently disposed sampling orifice external to the IMS. The operator may place a sample in the near vicinity of this external sampling orifice, and the ambient vapor may be drawn into the gas flow moving towards the ion source.

Sometimes molecules of interest undesirably adsorb onto surfaces in the sampling flow path. Therefore, it is sometimes useful to minimize unnecessary surfaces between the sampling orifice and the ion source. This is why, in some cases, the gas pump is often disposed in the gas flow stream following the ion source, rather than preceding the ion source.

SUMMARY OF THE INVENTION

According to the present invention, a gas sampling system for an ion mobility spectrometer includes a first gas pump providing a gas flow at a partial gas vacuum compared to ambient gas pressure, a second gas pump providing a gas flow at a partial gas pressure compared to the ambient gas pressure, a first orifice for the partial gas vacuum which is external to the ion mobility spectrometer, tubulation means connecting the first orifice to the ion mobility spectrometer, a second orifice for the partial gas pressure which is concentric and external to the first orifice, and gas deflection means for inducing a rotational cyclonic motion of the gas flow from the second orifice. The partial gas vacuum may be within 50 millimeters of mercury (50 Torr) of the ambient gas pressure. The partial gas pressure may be within 50 millimeters of mercury (50 Torr) of the ambient gas pressure. The gas deflection may be provided by vanes or by the inside surface of the second orifice.

According further to the present invention, a gas sampling system for an ion mobility spectrometer includes a first gas pump providing a gas flow at a partial gas vacuum compared to ambient gas pressure, a second gas pump providing a gas flow at a partial gas pressure compared to the ambient gas pressure, a first orifice for the partial gas vacuum which is external to the ion mobility spectrometer, tubulation means connecting the first orifice to the ion mobility spectrometer, a second orifice for the partial gas pressure which is concentric and external to the first orifice, gas deflection means for inducing a rotational cyclonic motion of the gas flow from the second orifice; and electrostatic field means for precipitating particles inside the tubulation means. The partial gas vacuum may be within 50 millimeters of mercury (50 Torr) of the ambient gas pressure. The partial gas pressure may be within 50 millimeters of mercury (50 Torr) of the ambient gas pressure. Gas deflection may be provided by vanes or by the inside surface of said second orifice. The electrostatic means may be provided by a cathode disposed substantially on the axis of the tubulation with an applied voltage greater than 3000 Volts.

According further to the present invention, a gas sampling system includes an ion mobility spectrometer having a sampling orifice and a fluid rotator that creates a cyclonic gas flow beyond the sampling orifice, the cyclonic gas flow having an outer rotary flow about an axis substantially parallel to the central axis of the sampling orifice and an inner flow substantially parallel to the central axis of the sampling orifice. The ion mobility spectrometer may operate at substantially ambient gas pressure. A gas pump may draw a gas flow through the sampling orifice and generate a vacuum within 50 millimeters of mercury (50 Torr) of the substantially ambient gas pressure. The fluid rotator may include at least one vane. The fluid rotator may include a rotation-inducing orifice surrounding the sampling orifice. The inside surface of the rotation-inducing orifice may deflect a gas flow into a cyclonic gas flow. The gas sampling system may also include a gas pump connected to the rotation-inducing orifice that creates a cyclonic gas flow. The gas sampling system may also include a precipitator that removes at least a portion of any entrained particles within the gas flow into the sampling orifice. The precipitator may be an electrostatic precipitator. The electrostatic precipitator may include a cathode disposed on or near the drift tube, the cathode applying a voltage greater than 3000 Volts. The axis of the cyclonic gas flow may rotate about a rotation axis perpendicular to its central axis. The axis of the cyclonic gas flow may rotate about a plurality of rotation axes perpendicular to its central axis.

According further to the present invention, a compound gas sampling system for an ion mobility spectrometer, includes a plurality of gas sampling systems as described herein, the gas sampling systems arranged so that adjacent cyclonic flows rotate in opposing directions.

The invention applies to an ion mobility spectrometer that uses an external sampling orifice to draw in vapors to be analyzed. In addition to this existing orifice, a coaxial orifice is provided which emits gas towards the object to be sampled. Said emitted gas is further deflected such that it is induced to move in a circular flow about the axis of the external sampling orifice. A further component of the motion is a net velocity away from the external sampling orifice. This type of flow is often referred to as a cyclone. The spinning motion results in a radially-outward directed centrifugal force that restrains the emitted gas flow from immediately being drawn radially inward into the partial vacuum of the external sampling orifice. Eventually, friction with the surrounding ambient gas will slow the emitted gas sufficiently that it will be drawn into the partial vacuum at some distance from the external sampling orifice. Depending on the flow of the emitted gas, this distance can be varied from near the external sampling orifice (low flow) to far from the external sampling orifice (high flow). The cyclonic motion in effect creates a tube consisting of a wall of moving gas that behaves like an extension of the tube that formed the external sampling orifice.

BRIEF DESCRIPTION OF THE DRAWING

The invention is described with reference to the several figures of the drawing, in which.

DETAILED DESCRIPTION

When operating conventional IMS systems, increasing the sample gas flow rate increases the volume of gas sampled in a given amount of time, which can result in more sensitive detection. However, a higher sample gas flow rate also increases the velocity of the gas through the ion source, and too high a velocity can interfere with the performance of the IMS. In addition, a sampling orifice having the general form consisting of the end of a hollow tube will draw gas from locations disposed both directly in front of the orifice as well as locations disposed to the side of the orifice. The partial vacuum supplied by the gas pump declines rapidly to ambient gas pressure within a short distance from the sampling orifice, because gas is flowing into the orifice from many directions.

In some circumstances, it is desirable for IMS instruments to be able to sample vapors at a distance from the external sampling orifice. Examples may include, but are not limited to, sampling of vapor from complex surfaces that contain many holes, crevices, or deep depressions, people and animals that prefer not to be rubbed by absorbent material, large three dimensional objects, textured materials such as cloth, surfaces that must be sampled in a short time, and surfaces in which surface rubbing by human operators is inconvenient or expensive.

In addition, the sampling orifice may become contaminated with vapor-emitting particles if the sample inadvertently contacts the orifice. Such contamination is particularly difficult to remove in a short period of time, thus preventing continuous operation of the instrument. Such contamination could be avoided if vapors could be sampled at a distance from the sampling orifice, but sampling from a distance tends to substantially dilute the sampled gas and thus to reduce sensitivity.

The distance where vapors may be sampled beyond the sampling orifice may be increased by increasing the sample gas flow rate, i.e., increasing the pumping speed. However, besides the interference with the performance of the ion source of the IMS caused by high velocity flow, this method dilutes the concentration of the desired sample vapor by mixing in a much larger volume of ambient gas. Therefore, the sensitivity of the IMS may decline if the sample gas flow rate is increased excessively.

The sampling of vapors with the ordinary sampling orifice is not highly directional. This is normally of little consequence in conventional detectors, since the volume being sampled must normally be disposed very near to the orifice, and directionality is provided by moving the orifice to another location.

Figure 1:
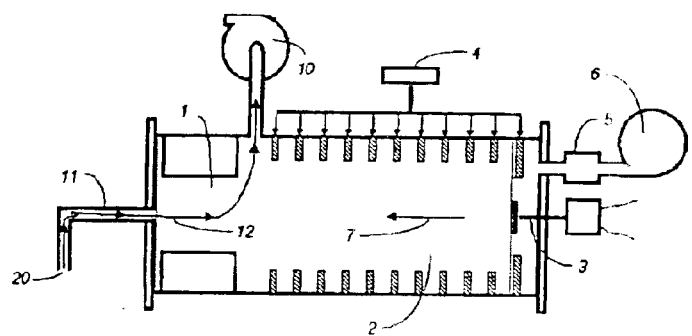
FIG. 1 is a schematic of the conventional IMS detector.

A conventional IMS is illustrated in FIG. 1. The IMS consists of an ion source 1, a drift tube 2, a current collector 3, a source of operating voltage 4 and a source of purified drift gas 5, possibly with its own gas pump 6. Conventionally, an IMS will already include a gas pump for gas sampling 10 and a tubular connection 11 between the ion source 1 and an external gas sampling orifice 20. Gas flow for the drift gas 7 moves through the drift tube 2. Sampling gas flow 12 moves from the external gas sampling orifice 20 through the tubular connection 11 and ion source 1 to the gas sampling pump 10. The IMS may operate at substantially ambient gas pressure (i.e., at ambient atmospheric pressure and at pressures relatively close to ambient atmospheric pressure).

Figure 2:
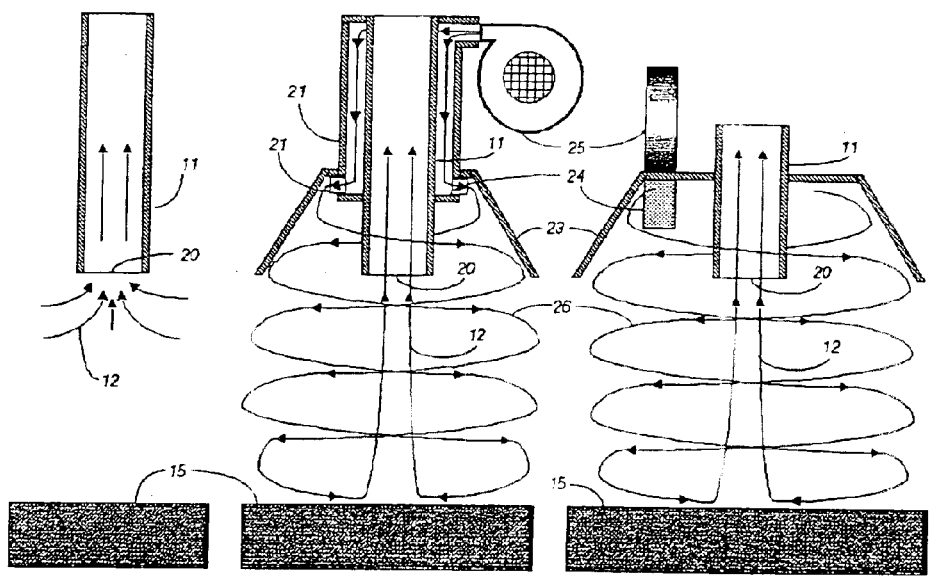
FIG. 2a is a schematic showing gas flow in a conventional gas sampling system not using a cyclonic flow.
FIG. 2b is a schematic showing a cyclone gas sampling system with a cone-shaped nozzle using deflection vanes.
FIG. 2c is a schematic showing a cyclone gas sampling system with a cone-shaped nozzle using tangential gas flow.

A conventional gas sampling system is shown in FIG. 2a. The gas pump for vacuum 10 may be disposed elsewhere and is not shown in the figure. The portion of the tubular connection 11 nearest the external gas sampling orifice 20 is shown. The sampling gas flow 12 shows that the volume of gas being sampled is disposed near to the external gas sampling orifice 20, and gas is being drawn into the orifice 20 over an angular range between substantially perpendicular to the axis of the orifice to on the axis of the orifice 20. When the target surface 15 is disposed at a distance greater than 1–2 times the diameter of the external gas sampling orifice 20, the quantity of sampled gas is either very small or highly diluted by the more abundant gas sampled from nearer the external gas sampling orifice 20.

A cyclone gas sampling system includes the following components as shown in FIGS. 2b and 2c. A partial vacuum relative to ambient gas pressure is supplied by a gas pump (not shown). The gas pump may be disposed at some distance from the cyclone gas sampling system with the vacuum being guided to the cyclone gas sampling system by means of a tubulation or conduit 11. The gas pump and corresponding tubulation 11 may already be part of an existing IMS. A partial pressure relative to ambient gas pressure is supplied by a gas pump 25. The gas pump 25 may be disposed at some distance from the cyclone gas sampling system with the pressure being guided to the cyclone gas sampling system by means of a tubulation or conduit 21. It is preferable that the pressure gas pump is separate from the vacuum gas pump to avoid cross-contamination of the sample gas between the two gas flows. The pressure gas flow 26 is induced to move in a circular, cyclonic motion away from the cyclone gas sampling system by a fluid rotator. The fluid rotator may include, for example, gas deflection vanes (shown in FIG. 2b), or a hollow, cylindrically or conically shaped orifice 23 concentric with the orifice for the partial vacuum 20. An alternate embodiment is to introduce the pressure gas flow through an orifice 24, which is oriented tangential to the hollow cylindrically or conically shaped orifice 23 and is deflected into a circular flow by means of the curvature of the inside wall. The pressure gas flow orifice 24 may be singular or a plurality of such orifices. The gas pump 25 may also be singular or a plurality of such pumps. Other means for inducing rotary flow of a gas, such as a turbine, are known in the art and are also included within the scope of the invention.

Figure 3:
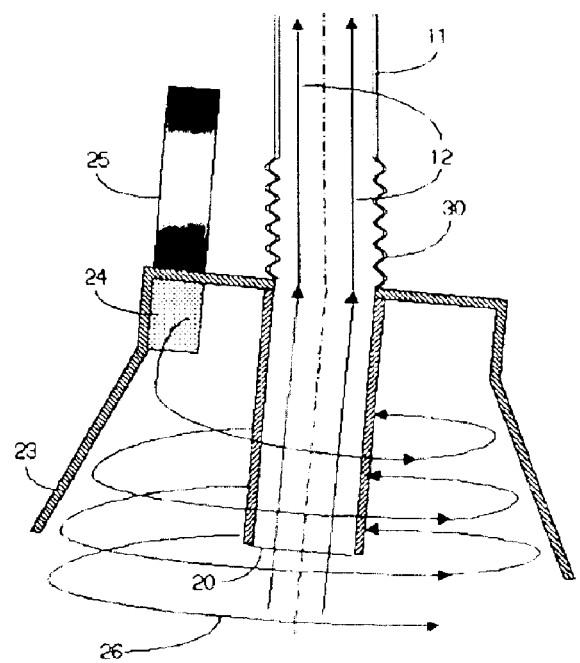
FIG. 3 shows a plurality of cyclones arranged in a rectilinear grid.

The axis of the emitted cyclonic gas flow defines the axis for guiding the partial vacuum from the external sampling orifice. If the axis of the emitted cyclonic flow is tilted over a small angular range, the partial vacuum due to the flow at the external sampling orifice follows this tilting motion, effectively scanning the position of the virtual gas sampling location. This characteristic is useful for sampling over a one dimensional stripe or a two dimensional surface area without moving the IMS from a fixed location. FIG. 3 shows one possible embodiment of a tilted cyclone in which the gas sampling tubulation 11 is flexible. Other possible embodiments would include, but not be limited to a ball joint within tubulation 11, a tilting cylindrical or conical surface 23 with the tubulation 11 fixed, and dynamic control of the relative velocities of a plurality of gas flows 26. As an alternative embodiment, one of the two axes of a two dimensional surface area could be scanned by mechanical movement of the object being scanned, perhaps along a track or moving belt. The second scan axis, perpendicular to the mechanically scanned axis, would be provided by tilting the cyclone orifice. This method is useful for minimizing the number of IMS instruments required to fully sample a given surface.

Cyclonic flow when combined with a vacuum may collect particles. The emitted gas flow generally exhibits a quasi-chaotic motion, which may dislodge larger particles from a surface. Once dislodged, the particles may become entrained in the gas flow towards the external sampling orifice. Depending on the application, such particles may or may not be desirable. For example, particles entering the ion source of the IMS may adhere to surfaces and continue to emit vapor for a long period of time, thus causing a continuous erroneous response. A limited range of particle sizes, about 0.5 to 10 micrometers in diameter, may be removed within the tubulation connecting the external sampling orifice to the ion source using electrostatic precipitation. Larger particles tend to be rejected radially outward due to the centrifugal force of the cyclone gas flow. Smaller particles cannot easily be rejected from the sampled gas.

The problem of contamination from particles may also be lessened by heating the tubulation connecting the external gas sample orifice to the ion source. The ion source may also be heated. Heating causes more rapid vaporization or sublimation of the contamination particles, thus shortening the time period of vapor emission and more rapidly cleansing the gas sampling system. As an alternate embodiment, the tubulation 11 may be designed to be an expendable component that is easily removed for cleaning or replacement.

Another advantage of the cyclone gas sampling method for IMS is that the system is light in weight, which is important for handheld sampling devices. Compared to existing sampling methods, one or more extra gas pumps are needed, but the power requirements are only a few Watts or less for most applications. An extra pump may also serve other functions in the IMS system, such as drawing cooling air from over a heated surface.

Figure 4:
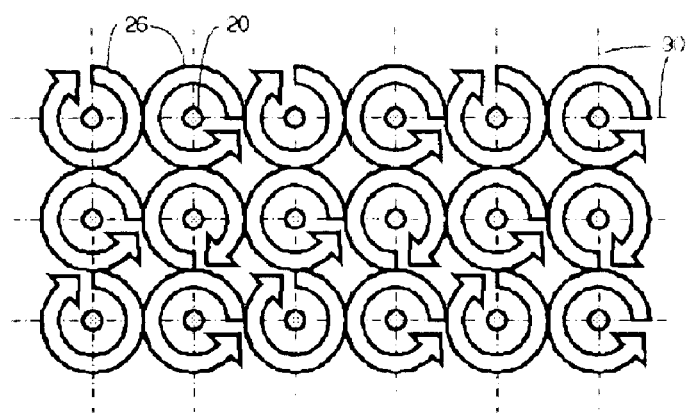
FIG. 4 shows an embodiment of a cyclone nozzle that may be scanned on at least one axis.

The cyclone sampling system may be utilized singly or by means of a plurality of cyclone sampling systems. The external gas orifice may be a single tubulation connected to a single ion source and IMS or there may be tubular branches leading from a single ion source to greater than one cyclone sampling system. Alternately, multiple ion sources plus IMS's plus cyclone sampling systems may be disposed proximally in order to more efficiently sample a larger surface area in a shorter period of time. FIG. 4 shows one possible layout of a plurality of IMS instruments. In this case a two dimensional grid is used in which the crossing points of the centering lines 40 is the location of an IMS instrument. The external gas sampling orifice 20 is indicated for each instrument. The circular direction of cyclone gas flow 26 is also indicated as preferably alternating clockwise and counterclockwise for neighboring instruments in order for the neighboring gas flows 26 to always be in the same direction.

When cyclone sampling systems are disposed proximally, neighboring cyclones preferably have rotational directions of the cyclonic gas flow that are oppositely oriented in order not to have the gas flows cancel each other at the boundary.

The gas flow of the gas emitted into the cyclone may be deflected into a circular flow by several possible means. Fractions of the total emitted gas flow may be selectively deflected by means of individually oriented vanes, such that the net resulting gas flow is circular. Alternatively, a hollow cone or cylinder may be employed with a gas flow entering the cone or cylinder at a tangential angle. The inside walls of the hollow cone or cylinder then act as the deflector, constraining the gas flow along a circular path while within the confines of the hollow cone or cylinder. When the emitted gas expands beyond the hollow cone or cylinder, the partial vacuum of the external sampling gas orifice provides the force required to constrain the emitted gas flow from moving tangentially away from the central axis.

Figure 5:
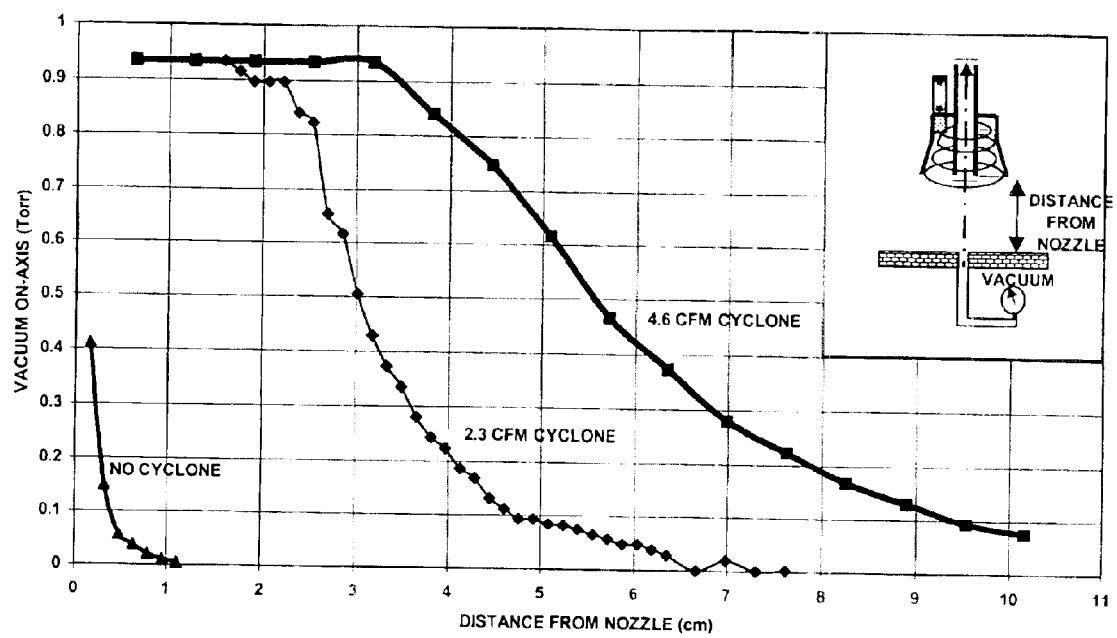
FIG. 5 shows partial vacuum measured on an axis of an external gas sampling orifice for no cyclone, for a 0.6 Watt cyclone with 2.3 cfm air flow, and for a 1.2 Watt cyclone with 4.6 cfm air flow.

FIG. 5 shows the measured vacuum below ambient gas pressure for three different flow rates of the cyclone gas. The external sampling gas orifice is 1.6 centimeters in diameter, and the greatest possible value for vacuum for the gas pump used in this measurement is about 1 Torr (1 millimeter of mercury) less than the ambient gas pressure. When no cyclone flow is present, 10% of maximum vacuum (0.1 Torr) occurs at a distance equal to about 0.25 times the external sampling gas orifice diameter. With a cyclone gas flow equal to 2.3 cubic feet per minute (cfm), the corresponding distance for 10% of maximum vacuum equals about 3.0 times the external sampling gas orifice diameter. With a cyclone gas flow equal to 4.6 cfm, the corresponding distance for 10% of maximum vacuum equals about 5.9 times the external sampling gas orifice diameter. This demonstrates that the length of the virtual extension of the gas sampling tubulation is proportional to the gas flow of the cyclone.

The IMS instrument described herein may incorporate other novel features, such as the improved laser ion source described in copending and commonly assigned U.S. Provisional Application 60/357,618, filed Feb. 15, 2002, or the electrostatic particle sampling system described in copending and commonly assigned U.S. Provisional Application 60/363,485, filed Mar. 12, 2002. These related provisional applications are incorporated by reference herein.

Other embodiments of the invention will be apparent to those skilled in the art from a consideration of the specification or practice of the invention disclosed herein. It is intended that the specification and examples be considered as exemplary only, with the true scope and spirit of the invention being indicated by the following claims.

What is claimed is:

1. A gas sampling system for an ion mobility spectrometer comprising:

a first gas pump providing a first gas flow at a partial gas vacuum compared to ambient gas pressure;

a second gas pump providing a second gas flow, different from said first gas flow, at a partial gas pressure compared to the ambient gas pressure;

a first orifice in communication with the first gas pump to provide the first gas flow toward the first gas pump, wherein the first gas flow is external to said ion mobility spectrometer;

tubulation means connecting said first orifice to said ion mobility spectrometer;

a second orifice in communication with said second gas pump to provide said second gas flow that rotates about and substantially surrounds said first gas flow to increase vacuum at a sampling location distal from the first orifice; and gas deflection means for inducing a rotational cyclonic motion of said second gas flow from said second orifice, wherein the gas sampling system samples said first gas flow for analysis in the ion mobility spectrometer.

2. A gas sampling system as in claim 1 wherein said partial gas vacuum is within 50 millimeters of mercury (50 Torr) of the ambient gas pressure.

3. A gas sampling system as in claim 1 wherein said partial gas pressure is within 50 millimeters of mercury (50 Torr) of the ambient gas pressure.

4. A gas sampling system as in claim 1 wherein said gas deflection is provided by vanes.

5. A gas sampling system as in claim 1 wherein said gas deflection is provided by the inside surface of said second orifice.

6. A gas sampling system for an ion mobility spectrometer comprising:

a first gas pump providing a gas flow at a partial gas vacuum compared to ambient gas pressure;

a second gas pump providing a gas flow at a partial gas pressure compared to the ambient gas pressure;

a first orifice for said partial gas vacuum which is external to said ion mobility spectrometer;

tubulation means connecting said first orifice to said ion mobility spectrometer;

a second orifice for said partial gas pressure which is concentric and external to said first orifice;

gas deflection means for inducing a rotational cyclonic motion of the gas flow from said second orifice; and electrostatic field means for precipitating particles inside said tubulation means.

7. A gas sampling system as in claim 6 wherein said partial gas vacuum is within 50 millimeters of mercury (50 Torr) of the ambient gas pressure.

8. A gas sampling system as in claim 6 wherein said partial gas pressure is within 50 millimeters of mercury (50 Torr) of the ambient gas pressure.

9. A gas sampling system as in claim 6 wherein said gas deflection is provided by vanes.

10. A gas sampling system as in claim 6 wherein said gas deflection is provided by the inside surface of said second orifice.

11. A gas sampling system as in claim 6 wherein said electrostatic means is provided by a cathode disposed substantially on the axis of said tubulation with an applied voltage greater than 3000 Volts.

12. A gas sampling system, comprising:

an ion mobility spectrometer having a sampling orifice into which a first gas flow is induced; and a fluid rotator that creates a cyclonic second gas flow that is different from the first gas flow and rotates about the first gas flow beyond the sampling orifice to increase vacuum at a sampling location distal from the sampling orifice, the cyclonic second gas flow having an outer rotary flow about an axis substantially parallel to the central axis of the sampling orifice, wherein the gas sampling system samples the first gas flow for analysis in the ion mobility spectrometer.

13. A gas sampling system, according to claim 12, wherein the ion mobility spectrometer operates at substantially ambient gas pressure.

14. A gas sampling system according to claim 13, wherein a gas pump draws a gas flow through the sampling orifice and generates a vacuum within 50 millimeters of mercury (50 Torr) of the substantially ambient gas pressure.

15. A gas sampling system according to claim 12, wherein the fluid rotator comprises at least one vane.

16. A gas sampling system according to claim 12, wherein the fluid rotator includes a rotation-inducing orifice surrounding the sampling orifice.

17. A gas sampling system according to claim 16, wherein the inside surface of the rotation-inducing orifice deflects a gas flow into a cyclonic gas flow.

18. A gas sampling system comprising:

an ion mobility spectrometer having a sampling orifice;

a fluid rotator that creates a cyclonic gas flow beyond the sampling orifice, the cyclonic gas flow having an outer rotary flow about an axis substantially parallel to the central axis of the sampling orifice and an inner flow substantially parallel to the central axis of the sampling orifice, wherein the fluid rotator includes a rotation-inducing orifice surrounding the sampling orifice; and a gas pump connected to the rotation-inducing orifice that creates a cyclonic gas flow.

19. A gas sampling system, comprising:

an ion mobility spectrometer having a sampling orifice into which a first gas flow is induced;

a fluid rotator that creates a cyclonic second gas flow that is different from the first gas flow and rotates about and substantially surrounds the first gas flow beyond the sampling orifice to increase vacuum at a sampling location distal from the sampling orifice, the cyclonic second gas flow having an outer rotary flow about an axis substantially parallel to the central axis of the sampling orifice; and a precipitator that removes at least a portion of any entrained particles within the first gas flow into the sampling orifice.

20. A gas sampling system according to claim 19, wherein the precipitator is an electrostatic precipitator.

21. A gas sampling system according to claim 20, wherein the electrostatic precipitator includes a cathode disposed on or near the drift tube, the cathode applying a voltage greater than 3000 Volts.

22. A gas sampling system according to claim 12, wherein the axis of the cyclonic gas flow is tilted.

23. A compound gas sampling system for an ion mobility spectrometer, comprising:

a plurality of gas sampling systems according to claim 12, the gas sampling having interconnected tubulation arranged so that adjacent cyclonic flows rotate in opposing directions.

* * * * *